(12) United States Patent
Gottschalk

(10) Patent No.: US 7,955,060 B2
(45) Date of Patent: Jun. 7, 2011

(54) PERISTALTIC PUMP

(75) Inventor: Andreas Gottschalk, Bergisch Gladbach (DE)

(73) Assignee: PFM Medical TPM GmbH (DE)

( * ) Notice: Subject to any disclaimer, the term of this patent is extended or adjusted under 35 U.S.C. 154(b) by 0 days.

(21) Appl. No.: 10/530,071

(22) PCT Filed: Oct. 4, 2003

(86) PCT No.: PCT/EP03/10998
§ 371 (c)(1),
(2), (4) Date: Jan. 12, 2006

(87) PCT Pub. No.: WO2004/033903
PCT Pub. Date: Apr. 22, 2004

(65) Prior Publication Data
US 2006/0110274 A1     May 25, 2006

(30) Foreign Application Priority Data
Oct. 4, 2002 (DE) .................. 102 46 469

(51) Int. Cl.
*F04B 43/08* (2006.01)
(52) U.S. Cl. .................. 417/477.1; 417/477.3; 604/153; 74/567
(58) Field of Classification Search .................. 417/474, 417/475, 476, 477.5, 477.3, 477.6, 477.1, 417/477.7, 477.8, 472; 604/153; 74/567, 74/569
See application file for complete search history.

(56) References Cited

U.S. PATENT DOCUMENTS

| | | | | |
|---|---|---|---|---|
| 2,877,714 A | * | 3/1959 | Leonard et al. | 417/475 |
| 3,981,633 A | | 9/1976 | Wall | |
| 4,746,279 A | | 5/1988 | Manella | |
| 4,755,168 A | * | 7/1988 | Romanelli et al. | 604/34 |
| 4,909,710 A | * | 3/1990 | Kaplan et al. | 417/53 |
| 4,954,046 A | | 9/1990 | Irvin et al. | |
| 5,018,945 A | | 5/1991 | D'Silva | |
| 5,088,904 A | | 2/1992 | Okada | |
| 5,152,680 A | | 10/1992 | Okada | |
| 5,165,873 A | | 11/1992 | Meijer | |
| 5,263,830 A | * | 11/1993 | Goi et al. | 417/474 |
| 5,558,507 A | * | 9/1996 | Magnus | 417/474 |

(Continued)

FOREIGN PATENT DOCUMENTS
DE     2526060 A1     6/1975

(Continued)

OTHER PUBLICATIONS

Concise Explanation of Relevance for DE 29805173 U1.

(Continued)

*Primary Examiner* — Charles G Freay
*Assistant Examiner* — Todd D Jacobs
(74) *Attorney, Agent, or Firm* — Knobbe Martens Olson & Bear LLP

(57) ABSTRACT

A pumping apparatus has a peristaltic drive device for pumping a medium through a line that has a compressible portion. The pump contains a one-piece shaft with offset cam segments and lamellae. The shaft may or may not include a core shaft or a continuous core region for an increase in stability. The continuous core region has cam segments offset with respect to one another and contiguous to one another. The ratio between the height and stroke of the lamellae is about 4:1 or less.

35 Claims, 11 Drawing Sheets

U.S. PATENT DOCUMENTS

Figure 1:
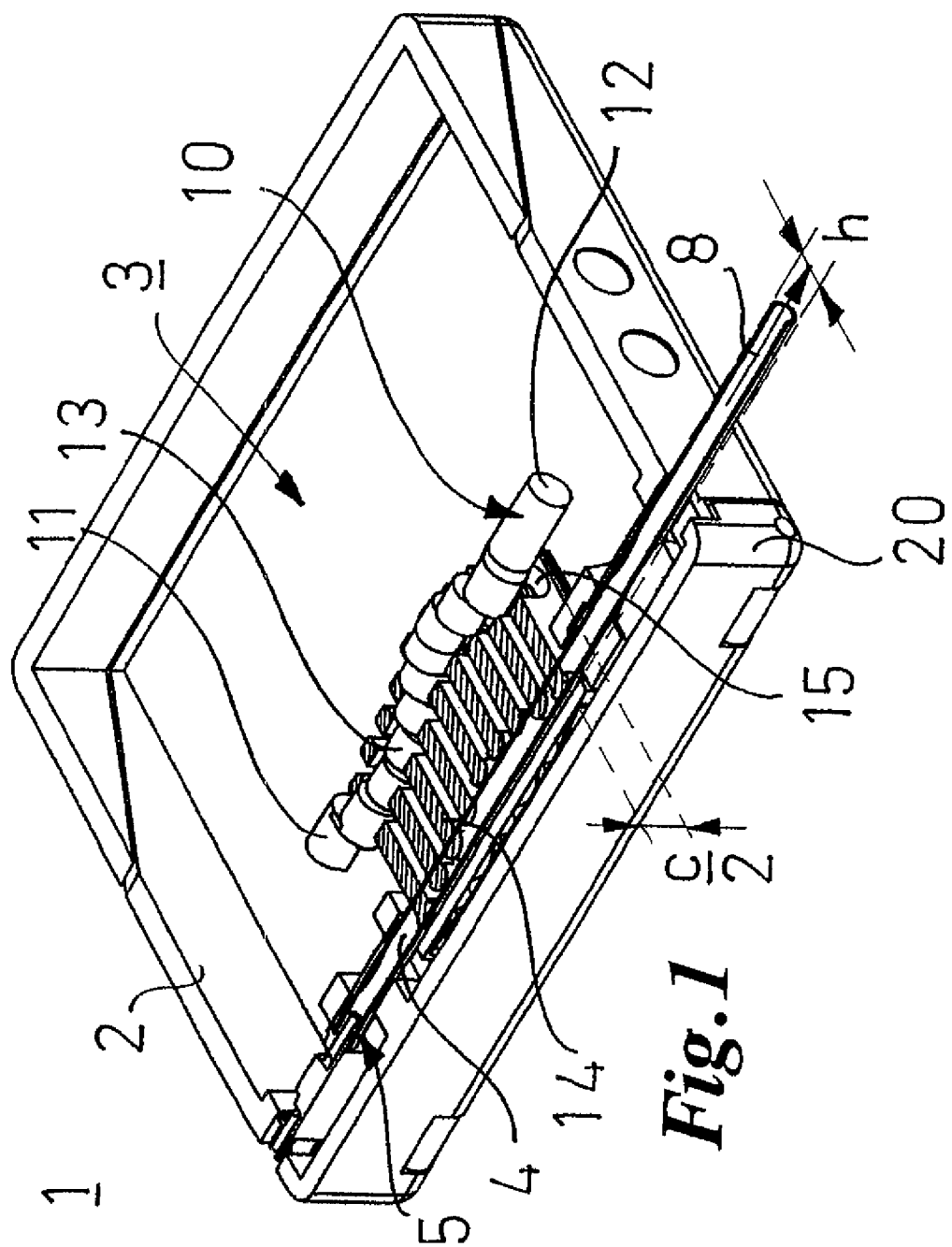

| | | | |
|---|---|---|---|
| 5,676,192 A * | 10/1997 | Itabashi et al. | 164/100 |
| 5,778,530 A * | 7/1998 | Nakamura et al. | 29/888.1 |
| 5,964,583 A * | 10/1999 | Danby | 417/474 |
| 6,289,764 B1 * | 9/2001 | Smith et al. | 74/567 |
| 6,394,771 B2 * | 5/2002 | Butterfield | 417/477.1 |
| 2006/0110274 A1 | 5/2006 | Gottschalk | |

FOREIGN PATENT DOCUMENTS

| | | |
|---|---|---|
| DE | 32 02 251 C1 | 8/1983 |
| DE | 3611643 C2 | 11/1986 |
| DE | 69008638 T2 | 7/1989 |
| DE | 69010194 T2 | 12/1989 |
| DE | 69018208 T2 | 12/1989 |
| DE | 69201966 T1 | 1/1991 |
| DE | 69303516 T2 | 9/1993 |
| DE | 9205733 U1 | 10/1993 |
| DE | 69201966 * | 11/1995 |
| DE | 298 05 173 U1 | 8/1998 |
| DE | 10246469 | 4/2004 |
| EP | 0410872 A1 | 1/1991 |
| EP | 0422855 | 4/1991 |
| EP | 560270 | 9/1993 |
| FR | 1470136 | 2/1966 |
| GB | 1081818 | 3/1965 |

OTHER PUBLICATIONS

Concise Explanation of Relevance for DE 3202251 A1.

* cited by examiner

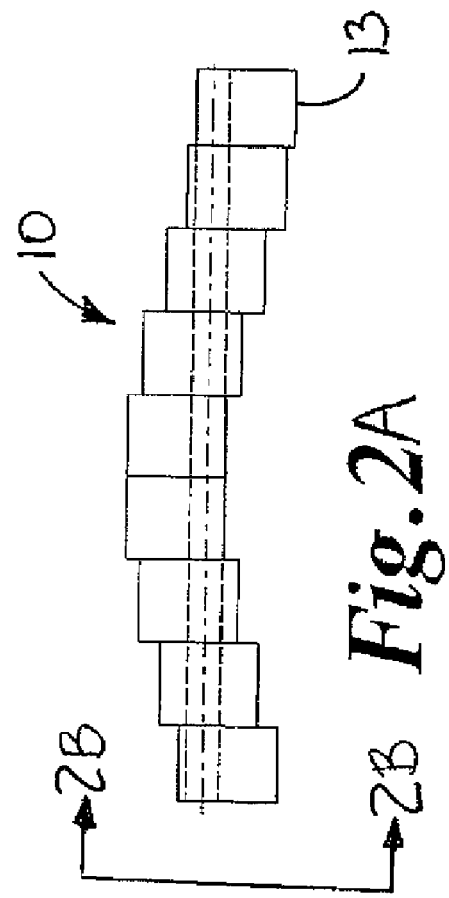
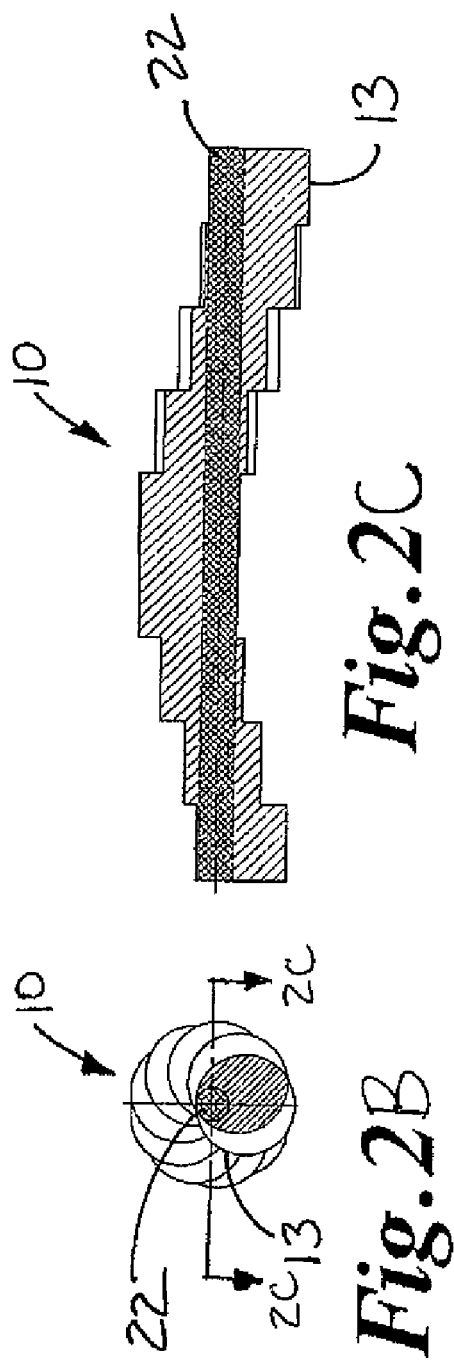

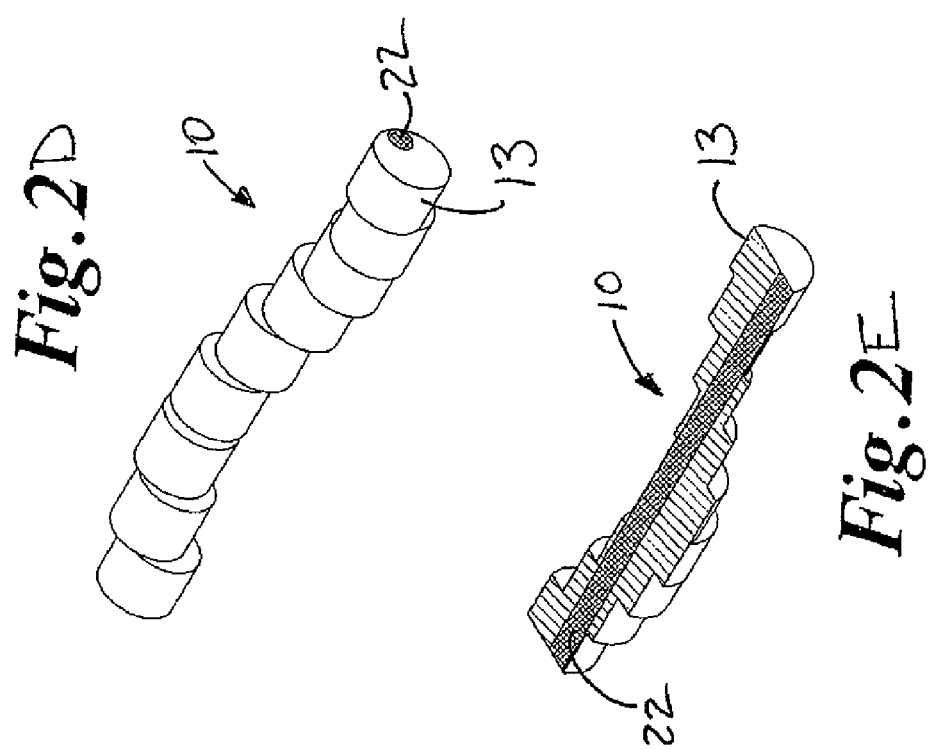

PERISTALTIC PUMP

BACKGROUND OF THE INVENTION

1. Field of the Invention

This invention relates to a pumping apparatus with a peristaltic drive device for pumping a medium through a line having at least one compressible portion, containing a shaft with cams arranged so as to be offset with respect to one another and with attached lamellae, a positive feed being provided for the lamellae.

2. Description of the Related Art

Pumping apparatuses with a peristaltic drive device for pumping medium through a hose are used, for example, as transfusion pumps and infusion pumps. Appliances of this type are known in the prior art. In most appliances, a return of the lamellae is generated by means of the hose elasticity. In this case, therefore, the hose elasticity must be selected such that it is possible for the lamellae to be pushed back by the hose. Normally, therefore, hoses made from silicone are used. If there is no return system provided, a jamming of the hose and an obstruction of the throughflow or an unwanted backflow may occur.

DE 692 01 966 T2 discloses, for example, the construction of a peristaltic pump for pumping a fluid from a fluid source through a line, a drive shaft being provided, with cam plates which are fastened eccentrically in a helical pattern to the drive shaft along this and can be rotated by means of the latter, and with finger plates which engage on the line and are coupled to the cam plates of the drive shaft. The drive shaft provided is a continuous core shaft, on which the cam plates are fastened. The finger plates each have a passage orifice, with which they are plugged onto the cam plates.

EP 0 422 855 B1 discloses a peristaltic pump with a continuous shaft having cams integrally formed on the latter. The cams have attached to them finger plates which each have an essentially rectangular passage orifice, into which the cams of round cross section engage. The finger plates or fingers press against a diaphragm, under which a hose is led through. The provision of four fingers is preferred in the patent. The individual fingers are of different length or cover a multiple of the distance which another finger covers. A distinction is made between pumping and pinching fingers, the pinching fingers being provided at a first and a third position and the pumping fingers being provided at a second and fourth position. The cams of the pinching fingers are provided on the shaft on one side only, and rotated at 180° with respect to one another, whereas the cams of the pumping fingers are arranged essentially in the same positioning on the shaft.

DE 690 18 208 T2 likewise discloses a peristaltic pump, in which a continuous drive shaft with cams attached to it and with fingers coupled to these is provided. An adjustable orientation means for defining an axis of rotation of the camshaft is provided, in order to linearise the fluid stream through a hose introduced into the linear peristaltic pump. The rotating camshaft is inclined by the adjustable orientation means until the fluid stream is essentially linear. The fingers are of essentially the same length and the cam discs are mounted eccentrically on the drive shaft.

DE 693 03 516 T2 discloses a linear peristaltic pump, in which a motor-operated cam shaft is mounted rotatably in a frame and is arranged parallel to a flexible and likewise mounted hose. The camshaft has at least three cams which are arranged so as to offset at an angle with respect to one another. For each cam, a tappet is provided, which is guided, between guide faces running parallel, in a direction running perpendicularly to the cam shaft and which has end faces for compressing the flexible hose. Each cam is provided with three arcuate portions, a first portion being provided for the pressure phase, a second portion being provided for holding the flexible hose in a closed state, and a third portion being provided for the rapid release of the hose.

A peristaltic pump with a rigid drive shaft is also known from DE 690 10 194 T2. A multiplicity of cams are provided on this drive shaft, too, each of the cams being offset angularly with respect to the in each case adjacent cam. A multiplicity of pressure fingers moving to and fro and cooperating with the cams are provided, these pressure fingers being driven by the cams. The rotational movement of the drive shaft is converted into a linear wave movement of the pressing fingers. A hose is enclosed between the pressure fingers and a pressure plate as an abutment, fluid movement being brought about by the pressure fingers.

DE 690 08 638 T2 discloses a transfusion pump which, via a drive mechanism, moves fingers which, by virtue of their Y-shape and one-sided fastening on one leg, can engage via the other leg on a hose and can compress the latter. The drive mechanism has a drive shaft, on which are attached twelve eccentric cam discs which come to bear against the respective finger extensions. As a result of the rotation of the drive shaft and of the cams located on it, the finger extensions are deflected, thus resulting likewise in the deflection of the legs which are at an angle to these and which bear against the hose, as a consequence of which the latter is compressed continuously and fluid conveyance is brought about.

DE 36 11 643 C2 discloses a peristaltic hose pump which is designed as a push-in unit. The hose pump has twelve first and second pressure elements which act as pressure members and which are arranged one behind the other. The first pressure element is in this case designed as a rectangular plate which has two projections on the side facing the second pressure element. The second pressure element is formed by two bar-shaped identically designed members. Twelve cam discs, against the control face of which a plate bears in each case, are arranged on a drive shaft at uniform intervals somewhat longer than the thickness of the members. Thus, once again, a continuous drive shaft with cam discs attached to it is provided.

DE 25 26 060 A1 discloses a peristaltic hose pump, in which the hose is led through a number of identical connecting rods arranged next to one another and is carried by these and extends through an orifice at one end of each connecting rod, the other end of which is mounted rotatably on a crankpin of a crankshaft bend. The connecting rods are set in an up-and-down movement by the crankshaft. The crankshaft bends are provided, offset at an angle with respect to one another, on the crankshaft. Since the hose is pushed through the connecting rods, it follows the up-and-down movement. The hose is fastened with its ends in a pump end and over its entire length encloses an immoveable circular rod which is centred in the said hose, in so far as no external stress acts on the hose due to the connecting-rod movement. During the progressive transverse wave movement of the hose, the latter comes to bear progressively on the rod, with the result that the ducts located above and below the rod are in each case closed and opened and the movement of fluid in the hose is thereby generated. This takes place without the pinching of the hose, but at a relatively high outlay because of the special shaping of the connecting rods having the lead-through orifices for the hose and because of the additional provision of the rod passing through the hose.

In addition to the abovementioned peristaltic pumps with drive shafts and cams or a crankshaft and bends, it is also known to provide a hose pump having a built-up shaft, as may be gathered, in particular, from DE 92 05 733 U1. The hose pump has slides which are arranged one behind the other and act with their end face in rhythmic alternation upon the hose. The slides are controlled by eccentric discs which are arranged so as to be angularly offset and which rotate about a common axis. The common axis is formed by axle stubs which project in each case on one side of a respective eccentric disc and are inserted into matching depressions of the in each case adjacent eccentric disc. Moreover, for further securing the axle stubs to one another, gudgeons are provided which are inserted in each case into holes of adjacent eccentric discs. The offset of the eccentric discs with respect to one another is formed by the respective offset of holes and gudgeons. This form of construction of a shaft or axle provided with eccentric discs proves to be highly complicated on account of the large number of individual parts which have to be produced so as to fit one another.

DE 298 05 173 U1 discloses a linear diaphragm pump, in which a conveying duct is provided, the shaft being worm-shaped.

U.S. Pat. No. 4,909,710 discloses a pumping apparatus with a one-piece shaft provided on its circumference with cam discs offset with respect to one another. The cam discs are in this case in one piece with the shaft. As a result, as with the cam discs attached to a shaft, it is likewise not possible to have a high throughflow rate in the case of a small type of construction of the pumping apparatus. There is the same restriction as, for example, in the prior art of DE 692 01 966 T2.

DE 32 02 251 C2 discloses an infusion hose pump which has a pumping member with a plurality of peristaltic slides moveable progressively and synchronously in a wavy manner transversely to the pumping zone. These are mounted rotatably at one end on crankpins. The crankpins are mounted eccentrically on a pump axis, so that, during operation, they displace the peristaltic slides to and fro transversely with respect to the pumping zone.

SUMMARY OF THE INVENTION

The object on which the present invention is based, then, is to form a less complicated pumping apparatus with a peristaltic drive device, which makes available as high a throughflow rate as possible, along with a small type of construction, and in which a pinching of a hose or of a line in the region of its at least one compressible portion can be avoided.

The object is achieved by means of a pumping apparatus according to the precharacterizing clause of claim 1, in that cams are cam segments and the ratio between lamella height and lamella stroke is about 4:1 or lower. In the case of a shaft for a pumping apparatus with a peristaltic drive device, the shaft being formed in one piece, the object is achieved in that the shaft has a design free of a core shaft, essentially without a continuous core region or, for an increase in stability, with a thin continuous core region having cam segments offset with respect to one another and contiguous to one another. Developments of the invention are defined in the dependent claims.

A pumping apparatus is thereby provided, having a peristaltic drive device which can have a small design, along with a high throughflow rate which, in particular, is around 8 l/h. This is not possible with small pump models of the prior art. The strokes necessary for such high throughflow rates cannot be achieved by providing a drive shaft having cam discs attached to it, such as described above in the prior art. With the pumping apparatuses according to the prior art, in which shafts guided during the forward and backward movement are provided, ratios between lamella height and lamella stroke of 7.5:1 and poorer are possible at best. The known lamellae have a height of, for example, 30 mm, with an orifice width of the orifices for leading through cam discs of 23 mm. Using the concepts of continuous drive shafts with attached cam discs according to the prior art, only strokes of 4 mm are possible in this case. Owing to the provision of positive guidance for the lamellae during the forward and backward movement, these always assume a defined state, and the risk of the pinching of the hose, which may result in damage to the latter, can be avoided. The lamellae, after being lowered onto the hose, are always drawn back again from the shaft. This benefit of positive guidance is advantageously possible in conjunction with a particularly high stroke of the lamellae. This is not possible with the pumping apparatuses of the prior art. In many instances, there, the elasticity of the hose brings about a return of the lamellae. Since, in the present invention, there is no fear of the risk of a pinching of a hose, despite the high strokes, hoses which are even less costly than the conventional silicone hoses can be used, for example PVC hoses. Operating costs are advantageously saved thereby.

Preferably, the shaft is without a core shaft. There is therefore no continuous shaft provided, which cam discs are attached or into which cam discs are integrated, as in U.S. Pat. No. 4,909,710. There is also no build-up shaft used, as disclosed in DE 92 05 733 U1. Instead, advantageously, a shaft formed essentially from cam segments placed against one another, without a central core shaft, is used. This is, however, produced in one piece, particularly preferably by the moulding method. It thereby becomes possible to provide the cam segments gradations with respect to one another that, even in the case of particularly small lamella dimensions, very high strokes can be achieved. The lamellae are in this case attached to the shaft. By a continuous core shaft being avoided and by cam segments merely being joined to one another, any desired shapes of the shaft can be achieved, which can preferably be adapted to the respective application. The shaft and lamellae preferably consist of plastic. The choice of the plastic may preferably depend on the strength requirements. Composite fibre materials and combinations of metals, plastics, fibre materials, etc. are also possible.

Preferably, the shaft has either no continuous core region or a thin continuous core region, in particular a continuous core region with a diameter of below 3 mm, in particular 2 mm or less or 1 mm or less. The stability of the shaft can be increased, in particular doubled, as a result. There is therefore no continuous core shaft provided, to which the cam discs are attached, but, instead, a continuous core region through which each cam segment of the shaft or each segment of the shaft runs. The buckling stability is thereby manifestly increased, as compared with an embodiment without a continuous core region, since a region which, although being narrow, is nevertheless continuous and stable is provided. In an embodiment essentially without a continuous core region, an even better, that is to say lower ratio of lamella height to stroke can be produced, although in this case the shaft has lower buckling stability on account of its free configuration. The ratio of the cam-segment diameter to the diameter of a continuous core region is preferably less than 4:1, in particular less than 3:1, in particular less than 2:1, in particular less than 1:1. In the case of a cam-segment diameter of 6 mm and a core-region diameter of 2 mm, for example, a ratio of 3:1 is obtained. The load-bearing capacity of such a shaft is determined by the size of the contact surfaces between the individual cam segments. In particular, if a continuous core region is omitted, an increase in stability can be achieved by an increase in the number of cam segments, since, as a result, the contact surface or connection surface between the individual cam segments can be enlarged owing to a smaller offset between the cam segments.

Preferably, an odd or an even number of cam segments is provided. Preferably, the cam segments are offset with respect to one another in such a way that only one cam segment is at a maximum distance from an imaginary center line of the shaft. It thereby becomes possible that, on the one hand, a hose introduced into the pumping apparatus is not pinched completely by the lamellae, but, on the other hand, without the fear of a backflow, is progressively compressed on one side in such a way that a fluid flow can be generated in the hose.

Preferably, the arrangement of the cam segments along the shaft is selected such that a pumping action in two directions (first direction and opposite second direction) is possible.

Particularly preferably, a uniform offset of the cam segments is provided, in particular an offset of 40° in the case of nine cam segments. Depending on the application, however, a non-uniform offset of the cam segments may also be provided, since these may be designed so as to offset with respect to one another in any desired way on account of the provision of a shaft without a core shaft. However, a more uniform offset of the cam segments contributes to a more symmetrical construction and to a more uniform pumping action.

Preferably, the pumping apparatus is used as in infusion pump, as a transfusion pump for dialysis or as a hose pump for another medical purpose. Precisely in the dialysis application, a destruction of the blood plasma, which would otherwise occur due to the pinching of the hose, can be prevented. It is important, in this context, merely that a volume can be enclosed in a leak-tight manner at the front and at the rear, that is to say at the first and at the last cam segment, and that the remaining lamellae or cam segments serve for the reduction in volume. The first and the last lamella are preferably switched as a valve and the remaining lamellae are preferably set in such a way that, in any position, at least a narrow gap remains between the walls of the hose acted upon by the lamellae. Moreover, advantageously, it is possible for the pumping apparatus to be utilized for a twin-duct system, in that lamellae are attached to the shaft on both sides and two hoses are led past the shaft on both sides.

Preferably, the shaft consists of a carbon fibre material, of a glass-fibre-reinforced polymer or of another stable and dimensionally stable material. Precisely when a carbon fibre material is used, high loads are possible, in particular loads of up to 20 kg. There is in this case no fear of the shaft breaking, even with a particularly unusual configuration of the shaft without a core-shaft region. The use of a gas-fibre-reinforced polymer likewise proves advantageous, particularly in the bearing region of the shaft, since a lubrication of the bearing is not possible and, when such a glass-fibre-reinforced polymer is used, this bearing requires no lubrication. Also, with the abovementioned materials or alternative stable and dimensionally consistent materials, an accuracy from the first to the last cam segment of, in particular, 5/100 mm can be achieved. Plain bearings or ball bearings are preferably used for mounting the shaft.

Advantageously, as regards the lamellae provided for use with such a pumping apparatus, the passage orifice corresponds in the longitudinal direction essentially to the outside diameter of cam segments of the shaft to which the lamellae can be or are attached. This ensures that the lamellae are reliably taken up by the shaft or its cam segments, without being jammed or slipping out of place on these. Particularly preferably, the passage orifice is essentially a long hole having a greater extent transversely to the longitudinal direction of the lamella. The dimension in the longitudinal direction of the long hole preferably corresponds essentially to the outside diameter circumscribed by the rotating cam segments. A free moveability of the lamella on the cam segment in the direction transverse to the longitudinal direction of the lamella is thereby possible, thus preventing the lamella from being jammed during the movement of the shaft, but at the same time ensuring that the said lamella is taken up by the shaft. The lamella therefore does not continue to exert a pinching action on the hose unintentionally, but, instead, is progressively drawn away from the latter again, without requiring its hose elasticity.

Preferably, a counterpressure plate for applying the line, in particular a hose, and for supporting the pressure exerted on the line or the hose by the lamellae is provided. Particularly preferably, the counterpressure plate is sprung within the housing of the pumping apparatus by means of one or more springs, in particular by means of barrel springs, leaf springs or another type of spring. It is thereby possible for the counterpressure on the line to be set individually, since, when the number and type of springs are changed, in each case different counterforces can be generated in combination with the counterpressure plate. Alternatively, the counterpressure plate may be provided, without springs, as a fixed element. The spring excursion can then be applied by means of the elasticity of the line or of the hose having a sufficiently large wall thickness.

Figure 2:
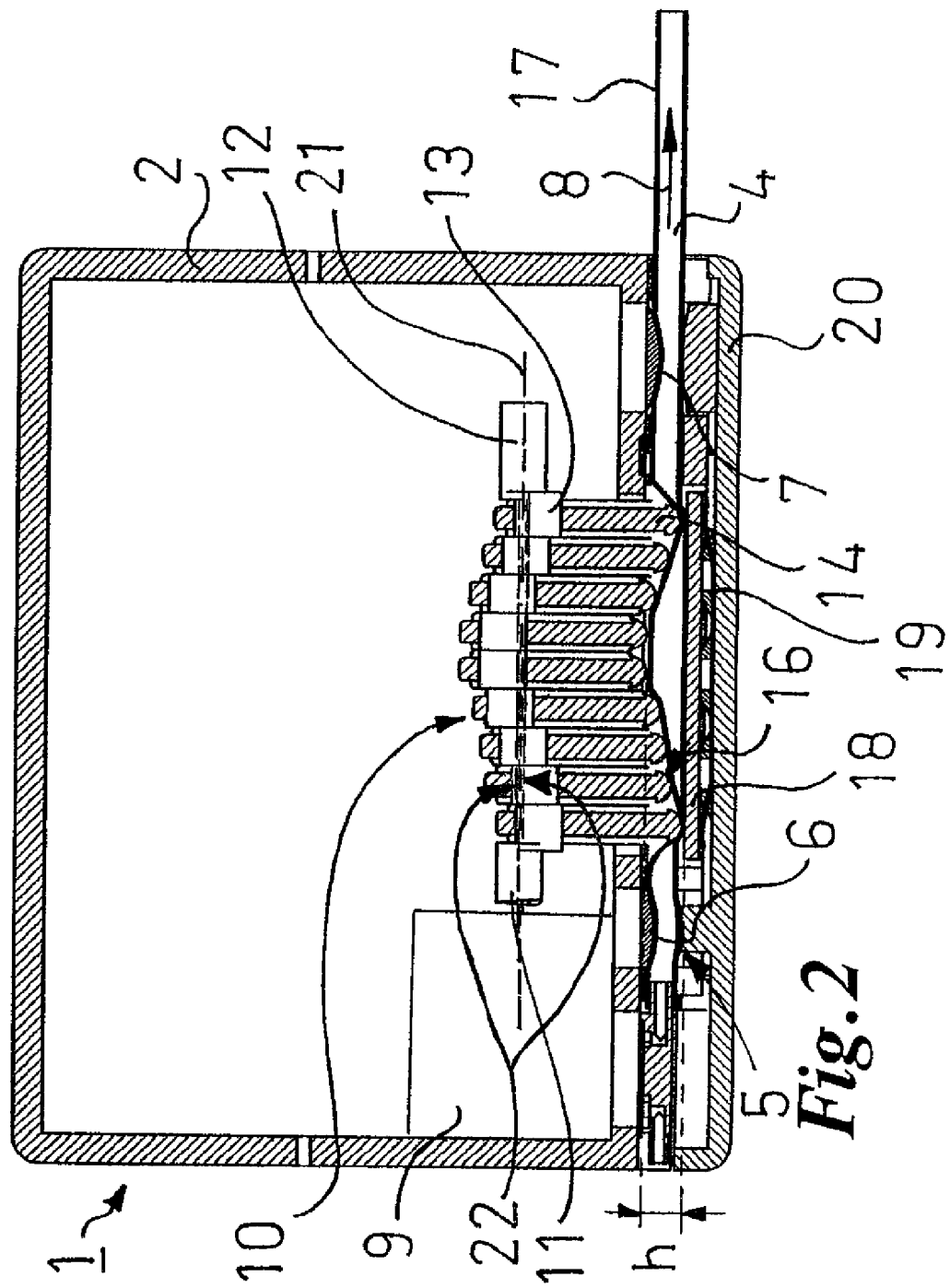

For a more detailed explanation of the invention, exemplary embodiments are described in more detail below with reference to the drawings in which:

FIG. 1 shows a perspective view of a first embodiment of a pumping apparatus according to the invention which is illustrated, partially cut away, for clarity, FIG. 2 shows a cross-sectional view of the embodiment of the pumping apparatus according to FIG. 1, FIG. 2A is a plan view of the cam segments from the shaft illustrated in FIG. 2 joined to one
another in an offset manner, FIG. 2B is an end view of the shaft from FIG. 2A and illustrates a continuous core region which is integral to the shaft.

Figure 3:
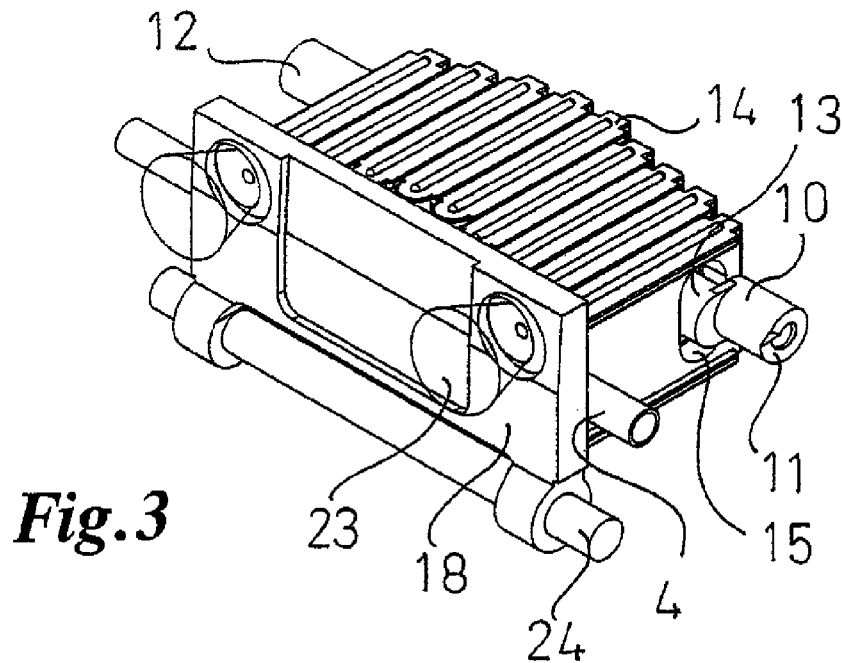
Figure 4:
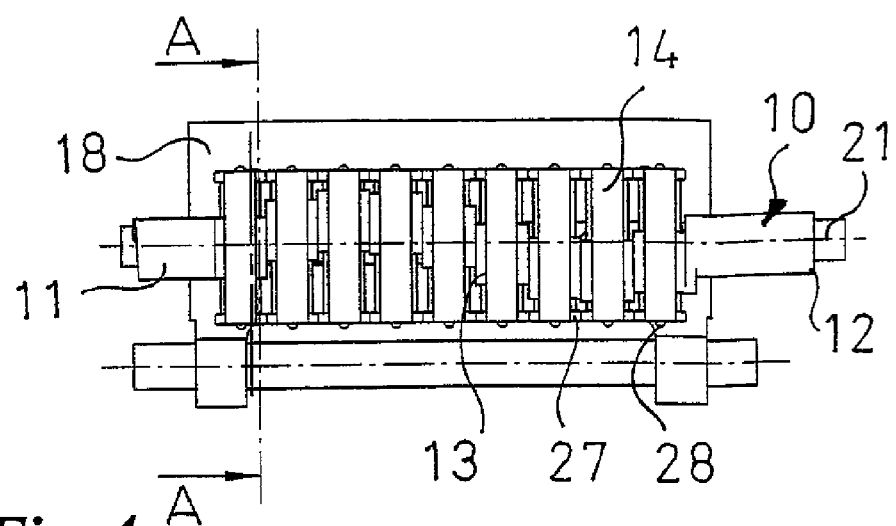
Figure 5:
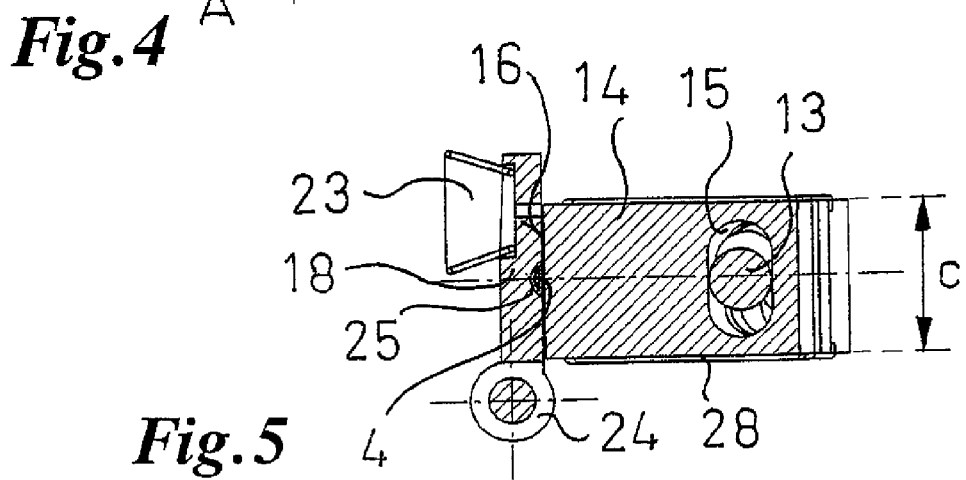
Figure 6:
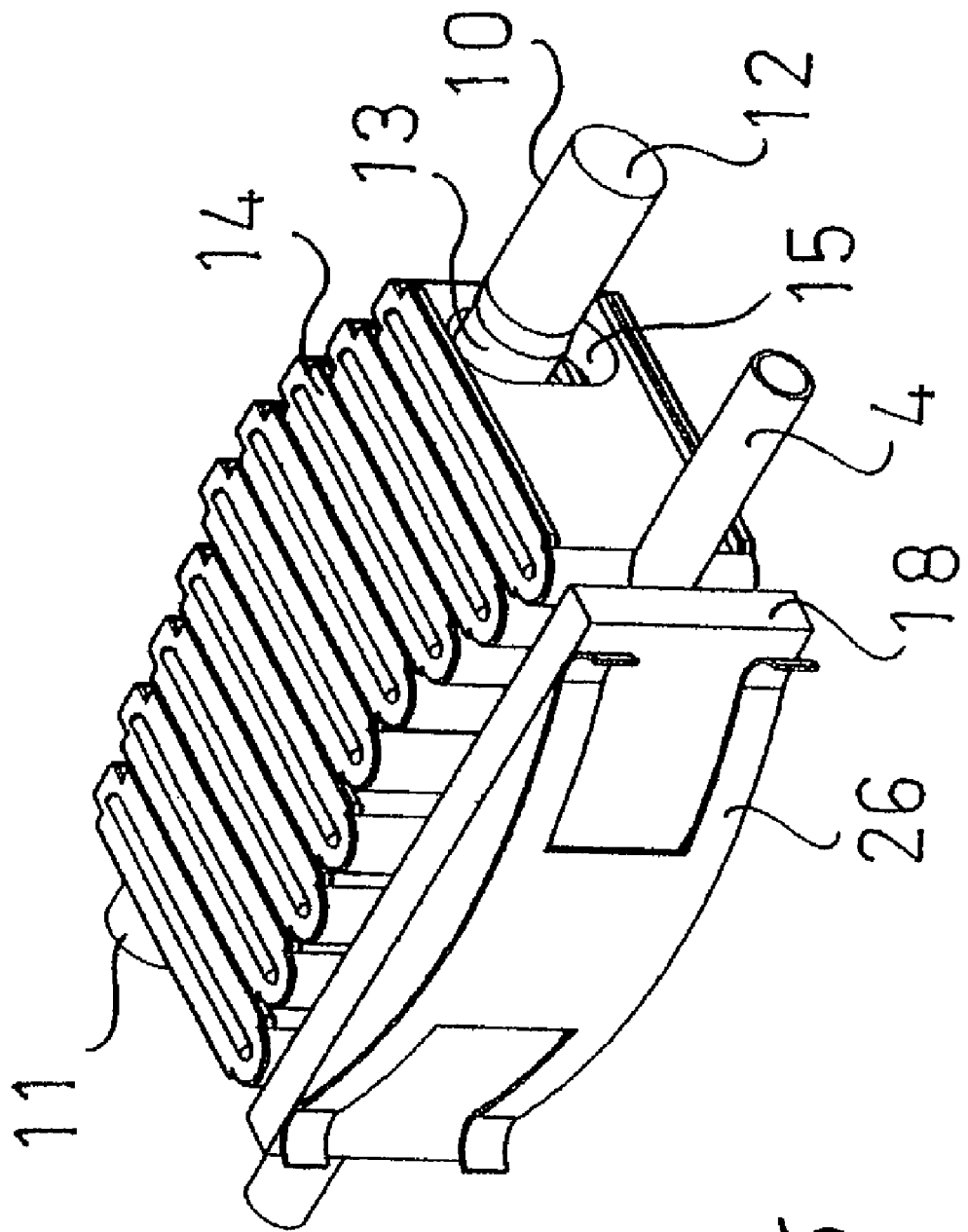
Figure 7:
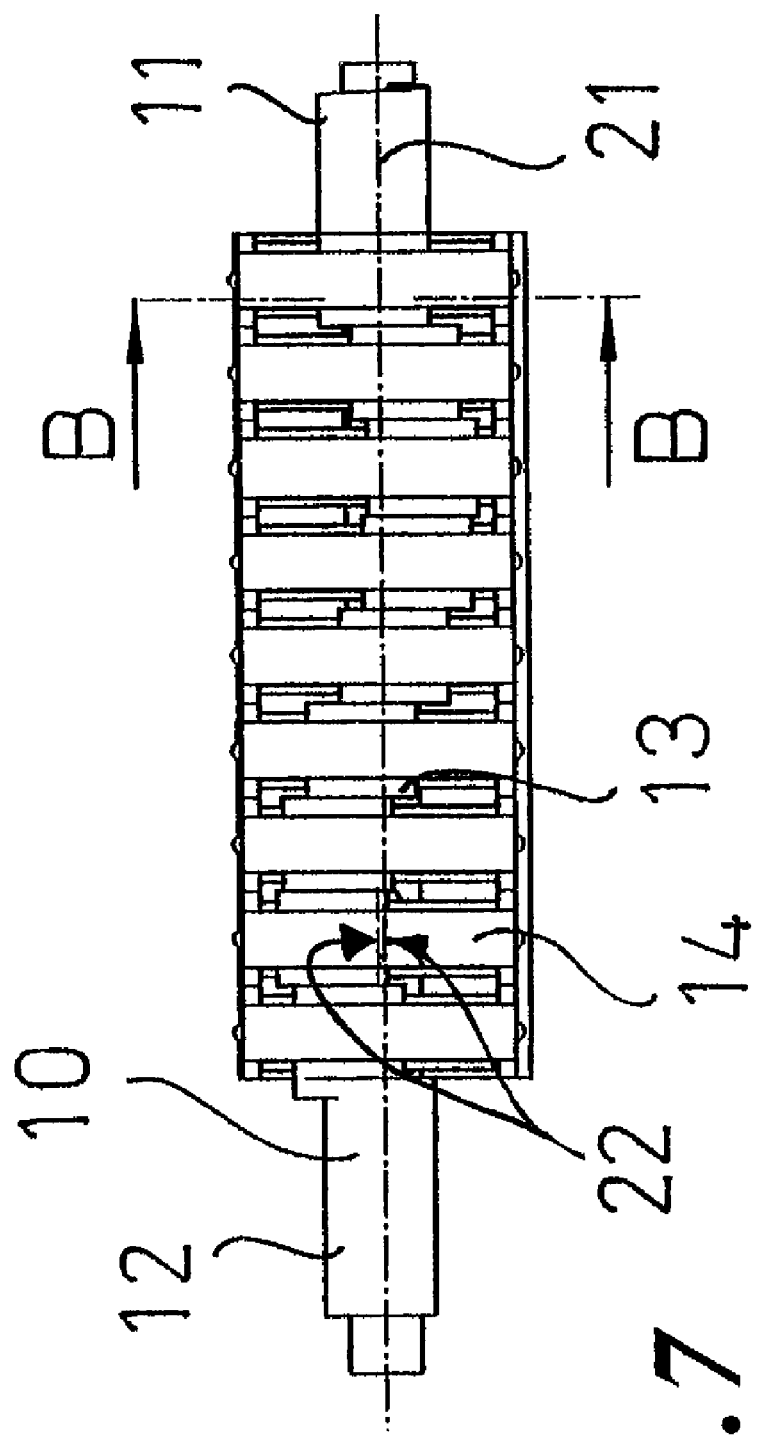
Figure 8:
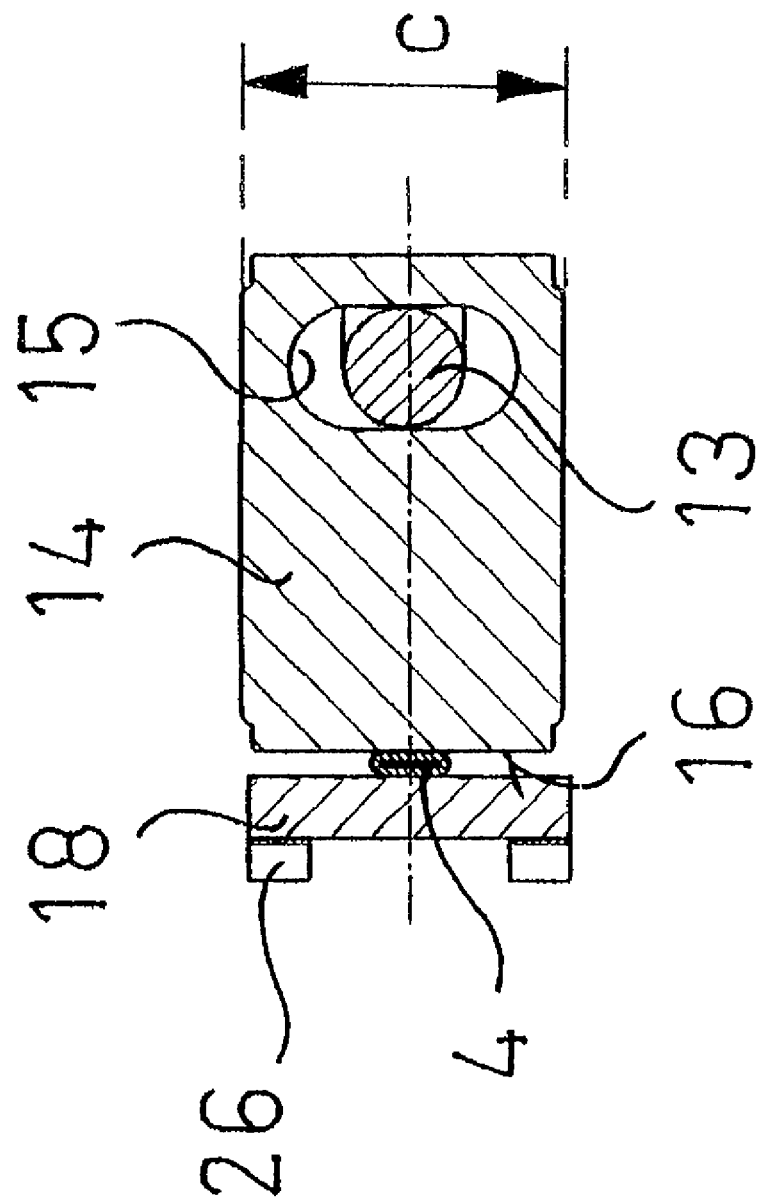
Figure 9:
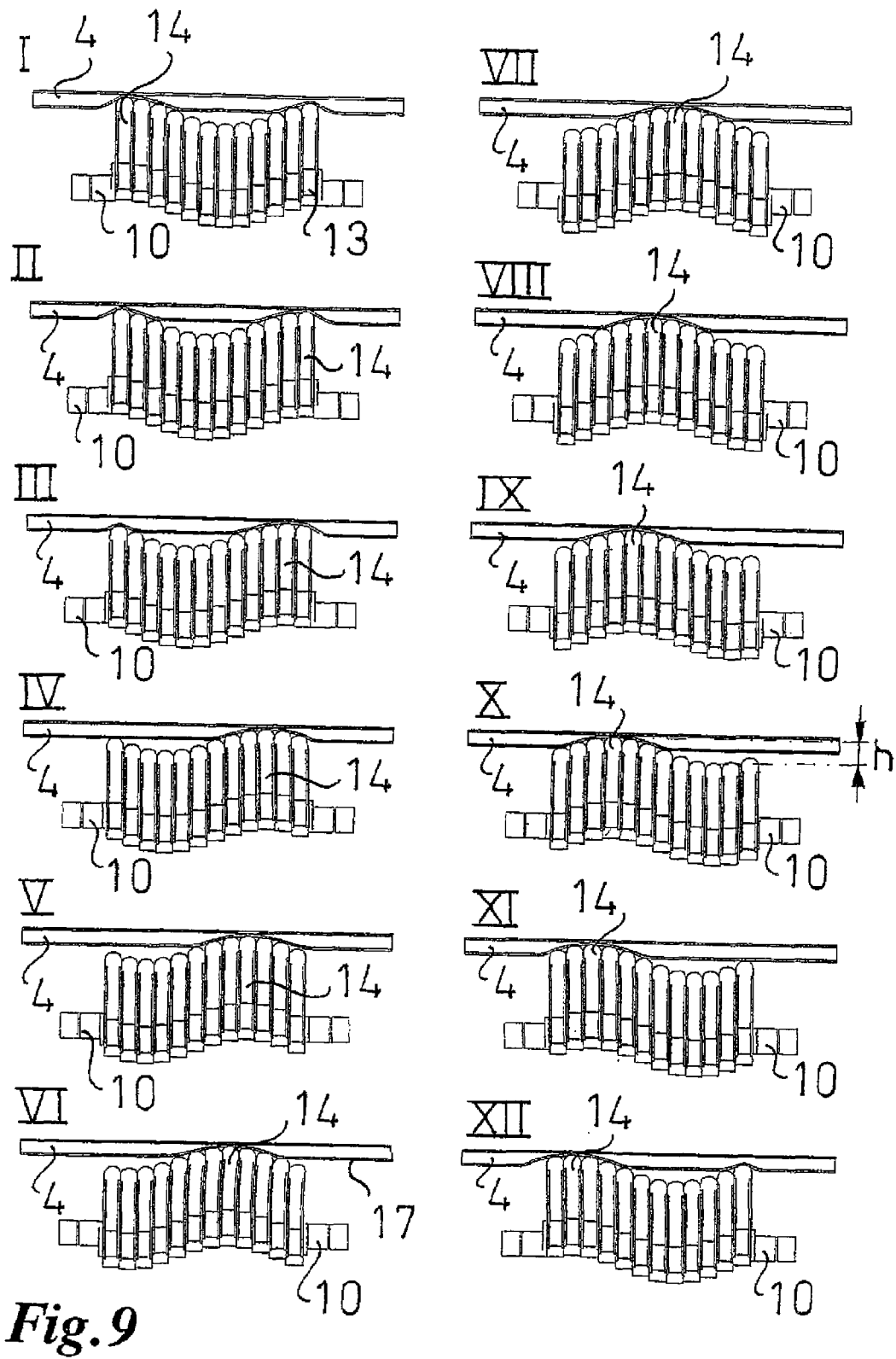
Figure 10:
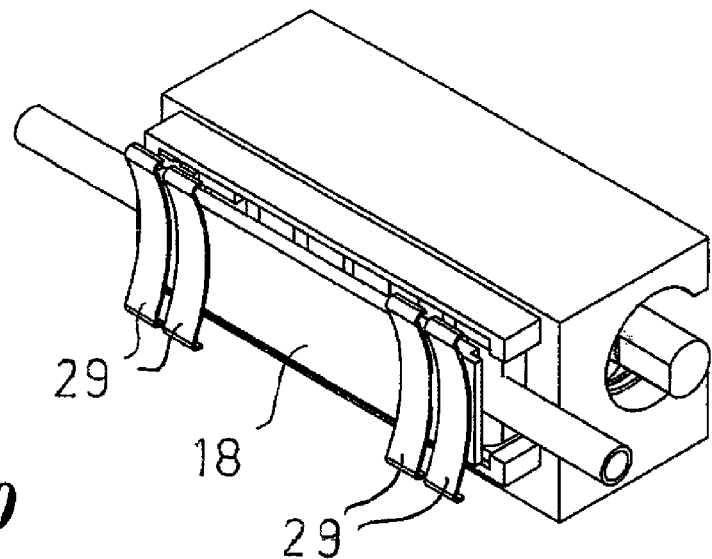
Figure 11:
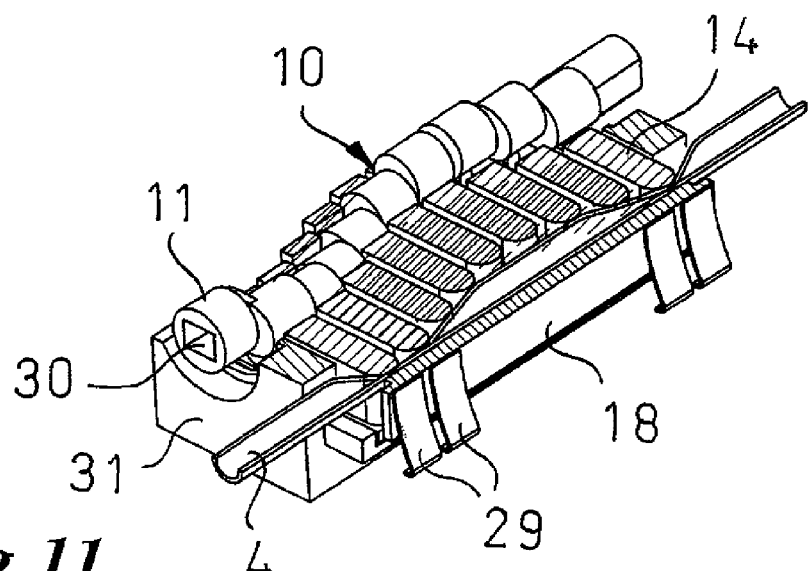
Figure 12:
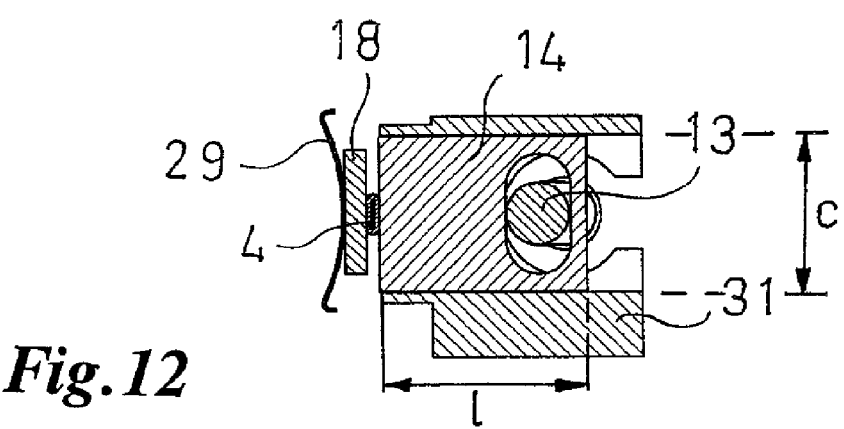

FIG. 2C is a cross-sectional view of the shaft illustrated in FIG. 2B taken along lines 2C-2C and illustrates the continuous core region, FIG. 2D is a perspective view of the cam segments from the shaft illustrated in FIG. 2 joined to one another in an offset manner, FIG. 2E is a cross-sectional view of the shaft illustrated in FIG. 2D and illustrates the continuous core region which is integral to the shaft, FIG. 3 shows a perspective view of a second embodiment of a pumping apparatus according to the invention, with the detail of the shaft, lamellae, a hose and a counterpressure plate, FIG. 4 shows a top view of the embodiment according to FIG. 3, FIG. 5 shows a sectional view through the embodiment according to FIG. 3 along the sectional line A-A in FIG. 4, FIG. 6 shows a perspective view of a further embodiment of the pumping apparatus according to the invention, with the detail of the shaft, lamellae, a hose and a counterpressure plate, FIG. 7 shows a top view of the embodiment according to FIG. 6, FIG. 8 shows a cross-sectional view of the embodiment according to FIG. 6 along the sectional line B-B according to FIG. 7, FIG. 9 shows an illustration of the progressive movement of the lamellae and the shaft during a pumping action in the sequence of twelve steps, FIG. 10 shows a perspective view of a further embodiment of the detail of the hose, shaft, lamellae and counterpressure plate of a pumping apparatus according to the invention, FIG. 11 shows a perspective sectional view of the embodiment according to FIG. 10, FIG. 12 shows a cross-sectional view of the embodiment according to FIG. 10 through a lamella, and FIGS. 13 to 16 show basic diagrams of various embodiments of shafts with different cam-segment diameters and with an identical stroke, with and without a continuous core region.

DETAILED DESCRIPTION OF THE PREFERRED EMBODIMENTS

FIG. 1 shows a perspective view of a first embodiment of a pumping apparatus 1 according to the invention, which is illustrated cut away. The pumping apparatus has a housing 2, in which is arranged a peristaltic drive device for generating a fluid stream in a hose 4. The hose preferably consists of an elastic material or has at least one portion which consists of a compressible material. The hose is introduced with this portion into an introduction region 5, as may also be gathered from the cross-sectional view in FIG. 2. Pressure and throughflow sensors 6, 7 are arranged upstream and downstream of the region of influence of the peristaltic drive device. The throughflow direction of the medium within the hose through the latter is indicated by an arrow 8.

The peristaltic drive device 3 has a drive motor 9 which engages on a shaft 10 at one end 11 of the latter. A second end 12 of the shaft is mounted within the housing, although this cannot be gathered in detail from the figures. The shaft 10 has cam segments 13 joined to one another in an offset manner. Lamellae 14 are attached to the cam segments. For this purpose, these lamellae have in each case a passage orifice 15. This may be gathered more clearly, in particular, from FIGS. 5 and 8. The lamellae engage with their end faces 16 on the outside 17 of the hose.

On the side located opposite the peristaltic drive device with respect to the hose is arranged a counterpressure plate 18 against which the end faces of the lamellae operate. The counterpressure plate is mounted resiliently, via a spring 19, in a flap 20 which can be swung open for the introduction of the hose. During the rotational movement of the shaft, the lamellae are moved toward the hose alternately on account of their offset with respect to one another and press the latter against the counterpressure plate 18. In order to prevent the hose from being pinched off or pinched excessively, which may also lead, inter alia, to a squeezing of blood plasma, the resilient mounting of the counterpressure plate in conjunction with the particular configuration of the shaft 10 is provided.

The shaft illustrated in FIGS. 1, 2, and 2A-2E, is without a core shaft, that is to say no continuous core shaft is provided, to which the cam discs are attached, but, instead, a shaft constructed in one piece from cam segments. Since a core shaft is omitted, any desired offset between the individual cam segments may be provided. In particular, the cam segments may be provided so far outside an imaginary center line 21 of the shaft 10 that with the provision of a core shaft, as is disclosed in the prior art, such a cam segment could even no longer be attached to the shaft (see FIGS. 15 and 16). An increase in the stroke h, as compared with a prior art, is thereby possible. At the same time, the lamellae may also have smaller dimensions, and, in particular, a smaller height c. The ratio between the lamella height and the lamella stroke is about 4:1 or better, in particular about 3.5:1, about 3:1, about 2.5:1, about 2:1, about 1.5:1, about 1:1 or less or, if appropriate, even somewhat more than 4:1. The ratios which lie between the ratios specified are also possible. In the prior art, only ratios between lamella height and lamella stroke in the case of guided shafts, in which the lamellae are drawn back by the shaft away from the hose to be compressed, of 7.5:1 or 8:1 and poorer are possible.

For example, the stroke h is 6 mm and the lamella height c is 13 mm thus resulting in a ratio of 2.17:1. In the prior art, lamellae with heights of 30 mm and with a stroke of 4 mm are customary, thus resulting in a ratio of 7.5:1. Thus, by means of the pumping apparatus 1 according to the present invention, a higher throughput of fluid volume through the hose, which, in particular, may be around 8 l/h, is possible. Where pumping apparatuses with such small dimensions are concerned, this is not possible in the prior art. In order to achieve these throughputs, very large dimensions would be required if the forms of construction of the prior art were used. However, precisely in medical applications, such as infusion and transfusion pumps, and in dialysis, such large dimensions should as far as possible be avoided, since the patients advantageously carry the pumping apparatuses on them. A small form of construction is possible with the pumping apparatus 1 according to the invention. Contrary to what is illustrated in the figures, the length of the lamellae may be very small. However, greater stability of the guidance of the forward and backward movement of the lamellae can be achieved by means of a longer lamella body.

In order to obtain a higher stability of the shaft 10, a core region 22 may be continuous, that is to say all the cam segments run through the latter. According to FIG. 2, the core region 22 is very small. For example the core region may amount to 0.8 mm, as a result of which, with the same form of construction, the lamella stroke is reduced from 6 mm to 5.2 mm. In this case, however, there would still be a ratio between lamella height and lamella stroke of 2.5:1. This is therefore still far better than in the prior art, along with an improved stability of the shaft 10.

As may be gathered from FIGS. 1 and 2, the cam segments 13 are offset essentially uniformly with respect to one another. As regards the nine cam segments illustrated in these figures, an offset of 40° between the cam segments is selected, so that, during a revolution of the shaft, each lamella comes to bear once with its face against the hose outside. Another offset between the cam segments and also any other number of cam segments may, of course, also be selected.

FIGS. 3 to 5 illustrate a further embodiment of part of the pumping apparatus. In this case, instead of individual springs, as in the embodiment according to FIG. 2, two barrel springs 23 are provided on the counterpressure plate 18, as may be gathered particularly clearly from FIGS. 3 and 5. The counterpressure plate is arranged so as to be pivotable away from the lamellae via a hinge 24. The hose lies in a recess 25 in the counterpressure plate, as shown in FIG. 5. In the illustration according to FIG. 5, which is a sectional view along the line A-A according to FIG. 4, the lamella 14 presses with its end face 16 against the counterpressure plate 18. By the recess 25 being provided, the hose cannot be compressed completely and pinched off at this point. However, preferably, the distance between the shaft or the cam segments in the outermost position and the counterpressure plate is set such that there is, in any case, no fear that the hose is pinched off. As can be seen particularly in FIGS. 4 and 5, lateral webs 27 in the longitudinal direction of the lamellae on the side faces of the latter serve for reducing the contact surface between the lamellae and consequently prefer a reduction of losses due to friction. Lateral webs 28 on the end faces of the lamellae serve for a reduction in friction.

As may be gathered particularly from FIG. 4, the shaft 10 shown in this embodiment is designed without a core shaft and without a core region 22. The eighth cam segment, counting from the left, in its extended position, is so far away from the center line 21 or lies with its outer face against this such that the core region becomes zero. The outer face of the cam segment may even lie outside the center line, below the center line 21 in FIG. 4, thus leading to an even greater stroke. The limit is in this case defined only by the stability of the shaft which should advantageously withstand even high loads due to large throughflow volumes.

According to FIGS. 3 and 5, the passage orifice 15 through the lamellae 14 is designed as a long hole. In this case, in the longitudinal direction of the lamellae, the orifice width of the passage orifice corresponds essentially to the outside diameter of the cam segment. In the direction arranged transversely to this, that is to say in the direction of the height of the lamella, the passage orifice opens very wide, so that sufficient moveability during the rotation of the shaft is afforded. The orifice width in this direction is determined by the distance between the outer faces of the cam segments and the center line 21. So that the lamellae move only linearly toward the hose and away from this, but not in the direction perpendicular thereto, the orifice width selected for the long hole is sufficiently large. A jamming of the lamella on the cam segment is avoided preferably by means of the dimensions and a suitable choice of material of the lamella and the cam segments or the shaft. For example, the shaft is produced from a plastic, in particular from carbon fibre material, in particular CFC. However, a glass-fibre-reinforced polymer may also be selected, this proving particularly advantageous with regard to the mounting of the shaft in the housing and on the drive unit, in particular the motor 9. Moreover, with these materials, a high accuracy is possible between the first and the last cam segment, with the result that jamming in the essentially identical passage orifices of the lamellae can be avoided. In this case, for example, accuracies of 5/100 mm are achieved. The lamellae likewise consist, for example, of a plastic. The choice of material for the lamellae and the shaft is preferably made dependent on the stresses which occur, in particular a plastic is selected as a function of the required strength.

A further alternative embodiment of the drive device of the pumping apparatus according to the invention is shown in FIGS. 6 to 8. In contrast to the embodiment according to FIGS. 3 to 5, a leaf spring 26, instead of the barrel springs 23, is provided for the resilient support of the counterpressure plate 18. With the leaf spring being provided, it is not absolutely necessary for the counterpressure plate to be designed as a swing hinge, but, instead, after the introduction of the hose, the counterpressure plate can be attached in front of the latter and the leaf spring subsequently pushed in. The counterpressure plate 18 according to this embodiment has no recess for the insertion of the hose or of part of the latter, as can be seen particularly in FIG. 8. Instead of the embodiment illustrated, for example, one, two or a plurality of thin leaf springs may be provided on the sides of the counterpressure plate.

FIG. 8 shows a section through the first lamella, as seen from the drive side, FIGS. 6 and 7 showing a drive unit rotated through 180°, as compared with FIGS. 3 and 4. It may in this case be gathered from FIG. 7, in the region of the eighth cam segment from the right, that a very small core region 22 is provided in the case of this shaft 10. The core region is indicated in this region only, so as not to impair the clarity of the rest of the illustration.

FIG. 9 illustrates the sequence of the progressive movement of the lamellae during a shaft revolution in 12 steps I to XII. In step I, the lamella which is first, as seen from the left and last, as seen from the right, to be precise the twelfth, pinches the hose 4. The first lamella, as seen from the right, is just before it pinches the hose. In step II, the reverse situation occurs, the last lamella, as seen from the right, has been drawn back a little, whereas the first lamella, as seen from the right, now presses onto the hose. A fluid volume can thereby be pinched reliably between the first and the last lamella, this being very important, particularly in dialysis, in order reliably to prevent the backflow of the fluid or medium to the patient.

In step III, the first and the last lamella have again moved back a little and the second lamella, as seen from the right, now pinches the hose. As the movement progresses, in step IV, the third lamella, as seen from the right, pinches the hose, and, in step V, the fourth lamella, as seen from the right, pinches the hose. The remaining lamellae in each case move progressively back a little. During the further rotation of the shaft 10, in the sixth step, the fifth lamella, as seen from the right, pinches the hose, and, in the seventh step, the sixth lamella, as seen from the right, pinches the hose. In the sixth step, the last lamella is drawn back to a maximum from the hose outside 17, and the first lamella, as seen from the right, is drawn back almost at a maximum from the latter. Between the lamella drawn back farthest from the hose surface and the lamella which is just pinching, the stroke h can be determined, that is to say the dimension by which the lamellae are moved to and fro at a maximum.

In step VIII, the seventh lamella, as seen from the right, pinches the hose, and, in step IX, the eighth lamella, as seen from the right, pinches the hose. In step VIII, the last lamella, as seen from the right, approaches the hose again, whereas the first lamella, as seen from the right, is now at a maximum distance from the outside of the latter. By contrast, in step IX, the first lamella also approaches the hose outside again. In step X, the ninth lamella, as seen from the right, pinches the hose and, in step XI, the tenth lamella, as seen from the right, pinches the hose. In this step, the last lamella, as seen from the right, is also involved in the pinching action again and already reduces the passage volume of the hose a little. In step XII, the eleventh lamella, as seen from the right, pinches the hose, and the first lamella, as seen from the right, begins again to reduce the hose volume in this region. The next step which then follows is step I again. In the case of a uniform offset of the cam segments of the shaft and therefore also of the lamellae with respect to one another, presupposing that the individual lamellae have identical dimensions, a sinusoidal pinching movement of the lamellae is thus generated, with the result that the fluid flow through the hose can be generated.

FIGS. 10 to 12 show a further embodiment of part of a pumping apparatus. In this, instead of only one leaf spring running longitudinally parallel to the hose, as shown in FIG. 6, pairs of leaf springs 29 are provided, which are arranged on the end faces transversely to the hose and which press onto the counterpressure plate 18. As described with regard to the previous figures, they exert a counterpressure with respect to the moving lamellae 14, as may be gathered particularly from FIG. 11. In this figure, the shaft 10 has, at one end 11, a square inner orifice 30, into which a sensor can be inserted. The latter is thereby arranged at the relevant point and at the same time in a space-saving and protective manner.

A design of the lamellae 14 is shown in longitudinal section in FIG. 12. Here, guidance is improved in that the lamellae are guided over their entire length in the housing part 31 receiving the lamellae. The guidance length is consequently maximised and guidance is improved.

Figure 13:
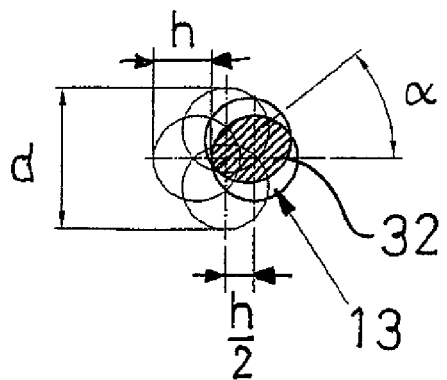

FIGS. 13 to 16 show various basic diagrams of shafts viewed from one cross-sectional side. In FIG. 13, the illustrated embodiment includes an internal continuous core region 22 (illustrated in FIGS. 2 and 2A-2E), and the cam segments 13 of the shaft 10 are offset with respect to one another by the amount of an angle α of 40° in each case. A relatively large contact surface 32 for increasing the stability of the shaft is thereby provided between the individual cam segments. Such a contact surface 32 is illustrated by broken lines in each of FIGS. 13 to 16.

In FIG. 13, the stroke h amounts to 4 mm, that is to say half the stroke h/2 to 2 mm. The cam segments have a diameter of 6 mm. The core region is selected such that the outside diameter d around which the rotating cam segments run amounts to 10 mm. In this embodiment, the core region has approximately a diameter of 2 mm, so that the ratio of the cam-segment diameter to the core-region diameter of 3:1 is obtained. The outside diameter d corresponds approximately to a lamella height or the inside diameter of the passage orifice 15 through a lamella. The ratio of the lamella height to the stroke would in this case therefore be around 3:1.

Figure 14:
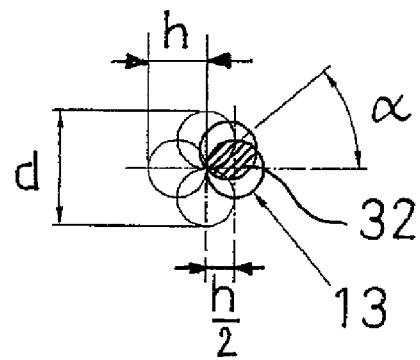

In the embodiment according to FIG. 14, a core region of about zero is provided, that is to say the cam segments are arranged next to one another in such a way that they do not overlap one another in the middle region during rotation. The offset again amounts to 40°. The cam-segment diameter is then 4 mm. The stroke is maintained at a constant 4 mm. However, the outside diameter d amounts only to 8 mm. The ratio of the cam-segment diameter to the diameter of the core region cannot be calculated, since there is no continuous core region provided. The ratio of lamella height to lamella stroke amounts to about 2.5:1.

Figure 15:
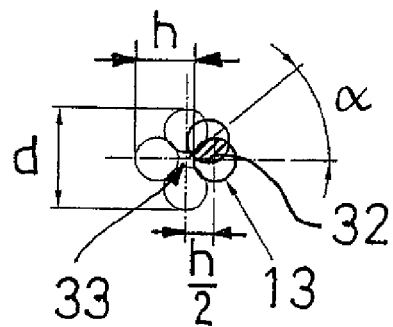

Considering, then, the embodiment according to FIG. 15, it is evident that the cam segments not only do not overlap or meet one another in a middle region, that is to say in the region of an imaginary center line 21, in the projection of the shaft into the plane, but, on the contrary, form an orifice 33 there. They rotate about this orifice. The cam-segment diameter may in this case be reduced even further, for example to 3 mm here. The selected stroke is again 4 mm. The outside diameter d amounts to 7 mm here. The offset between the individual cam segments continues to be 40°. There are therefore nine cam segments provided. The ratio of lamella height to lamella stroke thus amounts to 2.25:1.

Figure 16:
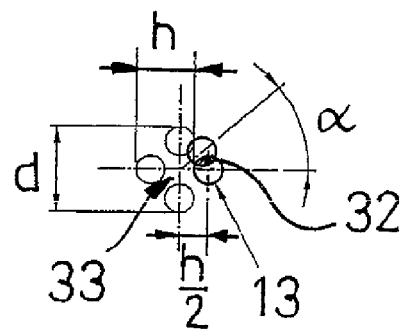

A further reduction in the cam-segment diameter is carried out in FIG. 16, where this amounts to only 2 mm. The stroke continues to be around 4 mm and the offset around 40°. The outside diameter is 6 mm. The ratio of lamella height to the lamella stroke thus amounts to about 2:1. Since the orifice 33 about which the cam segments rotate corresponds approximately to the cam-segment diameter, that is to say amounts to about 2 mm, the stability of the shaft 10 is not as great as, for example, in the embodiment according to FIG. 13 with a continuous core region or else according to FIG. 14 or 15. In order to enlarge the contact surfaces 32 between the cam segments, the number of cam segments may be increased, that is to say the offset reduced, as can be conceived in a simple way from FIG. 16. The choice of a somewhat higher ratio of lamella height to lamella stroke, such as, for example, in FIG. 13, constitutes a good compromise between as small mechanical structural elements as possible and as high a mechanical stability as possible.

In addition to the embodiments described above and depicted in the figures, others may also be formed, in which a positive guidance of the lamellae is provided in each case, that is to say a system for drawing the lamellae back from a line rhythmically to be pinched, and in which a high stroke can be achieved, as compared with the lamella size.

LIST OF REFERENCE SYMBOLS

1 Pumping apparatus
2 Housing
3 Peristaltic drive device
4 Hose
5 Introduction region
6 Pressure sensor
7 Throughflow sensor
8 Arrow
9 Motor
10 Shaft
11 First end
12 Second end
13 Cam segment
14 Lamella
15 Passage orifice
16 End face
17 Outside
18 Counterpressure plate
19 Spring
20 Flap
21 Center line
22 Core region
23 Barrel spring
24 Hinge
25 Recess
26 Leaf spring
27 Lateral web
28 Lateral web
29 Pair of leaf springs
30 Square inner orifice
31 Housing part
32 Contact surface
33 Orifice
h Stroke
c Lamella construction depth
l Lamella length
α Offset
d Outside diameter

The invention claimed is:

1. A pumping apparatus with a peristaltic drive device for pumping a medium through a hose having at least one compressible portion, containing a one-piece shaft rotating about a rotational axis and comprising a single homogenous piece of material with integral cams arranged so as to be offset with respect to one another and with attached lamellae, the shaft being configured to guide movement of the lamellae in both forward and backward directions, wherein the cams are cam segments and wherein the shaft is without a core region, wherein there exists an imaginary line running through the rotational axis in the region of the cams that does not contact the shaft.

2. The pumping apparatus according to claim 1, additionally comprising a counterpressure plate for applying the hose and for supporting the pressure exerted on the hose by the lamellae.

3. The pumping apparatus according to claim 2, wherein the counterpressure plate is sprung within a housing of the pumping apparatus by one or more springs.

4. A one piece shaft for a pumping apparatus with a peristaltic drive device, the shaft rotating about a rotational axis and comprising a single homogenous piece of material, wherein the shaft is designed without a core region, the shaft having integral cam segments offset with respect to one another and contiguous to one another, wherein there exists an imaginary line running through the rotational axis in the region of the cams that does not contact the shaft.

5. The shaft according to claim 4, wherein an odd or even number of cam segments is provided.

6. The shaft according to claim 4, wherein the cam segments are offset with respect to one another in such a way that only one cam segment is at a maximum distance from an imaginary center line of the shaft.

7. The shaft according to claim 6, wherein a uniform offset ($\alpha$) of the cam segments is provided.

8. The shaft according to claim 4, wherein the shaft comprises a plastic.

9. A method for pumping a medium through a hose having at least one compressible section, the method comprising:
providing a pumping apparatus with a peristaltic drive device containing a one-piece shaft rotating about a rotational axis and comprising a single homogenous piece of material, the shaft being without a core region, having integral cams arranged so as to be offset with respect to one another and with attached lamellae, the shaft being configured to guide movement of the lamellae in both forward and backward directions, the cams being offset with respect to one another and contiguous to one another, wherein there exists an imaginary line running through the rotational axis in the region of the cams that does not contact the shaft;
progressively compressing the hose on one side by the lamellae without completely pinching the hose; and
generating a fluid flow in the hose.

10. The method according to claim 9, further comprising pinching the hose so that a volume can be enclosed in a leak-tight manner at the first and at the last cam segment, and that the remaining lamellae serve for the reduction in volume.

11. The method according to claim 10, wherein the first and the last lamella are switched as a valve and the remaining lamellae are set in such a way that, in any position, at least a narrow gap remains between the walls of the hose acted upon by the lamellae.

12. The method according to claim 9, further comprising pumping in two directions, a first direction and an opposite second direction.

13. The method according to claim 9, further comprising generating a sinusoidal pinching movement of the lamellae for generating the fluid flow through the hose when the cam segments have a uniform offset.

14. An infusion pump comprising:
a peristaltic drive device for pumping a medium through a hose having at least one compressible portion, containing a one-piece shaft rotating about a rotational axis and comprising a single homogenous piece of material with integral cams arranged so as to be offset with respect to one another and with attached lamellae, the shaft being configured to guide movement of the lamellae in both forward and backward directions, wherein the cams are cam segments, and wherein the shaft is without a core region, wherein there exists an imaginary line running through the rotational axis in the region of the cams that does not contact the shaft.

15. A transfusion pump comprising:
a peristaltic drive device for pumping a medium through a hose having at least one compressible portion, containing a one-piece shaft rotating about a rotational axis and comprising a single homogenous piece of material with integral cams arranged so as to be offset with respect to one another and with attached lamellae, the shaft being configured to guide movement of the lamellae in both forward and backward directions, wherein the cams are cam segments, and wherein the shaft is without a core region, wherein there exists an imaginary line running through the rotational axis in the region of the cams that does not contact the shaft.

16. A hose pump for medical use comprising:
a peristaltic drive device for pumping a medium through a hose having at least one compressible portion, containing a one-piece shaft rotating about a rotational axis and comprising a single homogenous piece of material with integral cams arranged so as to be offset with respect to one another and with attached lamellae, the shaft being configured to guide movement of the lamellae in both forward and backward directions, wherein the cams are cam segments, and wherein the shaft is without a core region, wherein there exists an imaginary line running through the rotational axis in the region of the cams that does not contact the shaft.

17. The pumping apparatus of claim 1, wherein the ratio between the lamella height (c) and lamella stroke (h) is from about 4:1 to 1:1.

18. The shaft according to claim 4, wherein the cam segments define a continuous core orifice in the region of a center line.

19. A pumping apparatus with a peristaltic drive device for pumping a medium through a hose having at least one compressible portion, containing a one-piece shaft rotating about a rotational axis and comprising a single homogenous piece of material with integral cams arranged so as to be offset with respect to one another and with attached lamellae, the shaft being configured to guide movement of the lamellae in both forward and backward directions, wherein the cams are cam segments and wherein the shaft has a continuous core region having a diameter less than 3 mm, and wherein there exists a first imaginary cylinder of a diameter of less than 3 mm arranged along an imaginary line running through the rotational axis in the region of the cams that is contained within the shaft and a second imaginary cylinder of 3 mm or less arranged along an imaginary line running through the rotational axis in the region of the cams that is not contained within the shaft.

20. The pumping apparatus according to claim 19, additionally comprising a counterpressure plate for applying the hose and for supporting the pressure exerted on the hose by the lamellae.

21. The pumping apparatus according to claim 20, wherein the counterpressure plate is sprung within a housing of the pumping apparatus by one or more springs.

22. The pumping apparatus according to claim 19, wherein the arrangement of the integral cams defines an outside diameter and a stroke and wherein the ratio between the outside diameter and the stroke is less than 4:1.

23. A one piece shaft for a pumping apparatus with a peristaltic drive device, the shaft rotating about a rotational axis and comprising a single homogenous piece of material, wherein the shaft is designed with a continuous core region having a diameter less than 3 mm, the shaft having integral cam segments offset with respect to one another and contiguous to one another, and wherein there exists a first imaginary cylinder of a diameter of less than 3 mm arranged along an imaginary line running through the rotational axis in the region of the cams that is contained within the shaft and a second imaginary cylinder of 3 mm or less arranged along an imaginary line running through the rotational axis in the region of the cams that is not contained within the shaft.

24. The shaft according to claim 23, wherein an odd or even number of cam segments is provided.

25. The shaft according to claim 23, wherein the cam segments are offset with respect to one another in such a way that only one cam segment is at a maximum distance from an imaginary center line of the shaft.

26. The shaft according to claim 25, wherein a uniform offset ($\alpha$) of the cam segments is provided.

27. The shaft according to claim 23, wherein the shaft comprises a plastic.

28. A method for pumping a medium through a hose having at least one compressible section, the method comprising:
   providing a pumping apparatus with a peristaltic drive device containing a one-piece shaft rotating about a rotational axis and comprising a single homogenous piece of material, the shaft having a continuous core region with a diameter less than 3 mm, having integral cams arranged so as to be offset with respect to one another and with attached lamellae, the shaft being configured to guide movement of the lamellae in both forward and backward directions, the cam segments being offset with respect to one another and contiguous to one another, and wherein there exists a first imaginary cylinder of a diameter of less than 3 mm arranged along an imaginary line running through the rotational axis in the region of the cams that is contained within the shaft and a second imaginary cylinder of 3 mm or less arranged along an imaginary line running through the rotational axis in the region of the cams that is not contained within the shaft;
   progressively compressing the hose on one side by the lamellae without completely pinching the hose; and
   generating a fluid flow in the hose.

29. The method according to claim 28, further comprising pinching the hose so that a volume can be enclosed in a leak-tight manner at the first and at the last cam segment, and that the remaining lamellae serve for the reduction in volume.

30. The method according to claim 29, wherein the first and the last lamella are switched as a valve and the remaining lamellae are set in such a way that, in any position, at least a narrow gap remains between the walls of the hose acted upon by the lamellae.

31. The method according to claim 28, further comprising pumping in two directions, a first direction and an opposite second direction.

32. The method according to claim 28, further comprising generating a sinusoidal pinching movement of the lamellae for generating the fluid flow through the hose when the cam segments have a uniform offset.

33. A pumping apparatus with a peristaltic drive device for pumping a medium through a hose having at least one compressible portion, containing a one-piece shaft rotating about a rotational axis and comprising a single homogenous piece of material with integral cams arranged so as to be offset with respect to one another thereby defining an outside diameter and a stroke, and with attached lamellae, the shaft being configured to guide movement of the lamellae in both forward and backward directions, wherein the cams are cam segments, and wherein the ratio between the outside diameter and the stroke is less than 4:1, and wherein there exists an imaginary line running through the rotational axis in the region of the cams that does not contact the shaft.

34. The pumping apparatus of claim 33, wherein the ratio between the outside diameter and the stroke is less than 3:1.

35. The pumping apparatus of claim 33, wherein the ratio between the outside diameter and the stroke is less than 2:1.

* * * * *

UNITED STATES PATENT AND TRADEMARK OFFICE
CERTIFICATE OF CORRECTION

| | | |
|---|---|---|
| PATENT NO. | : 7,955,060 B2 | Page 1 of 1 |
| APPLICATION NO. | : 10/530071 | |
| DATED | : June 7, 2011 | |
| INVENTOR(S) | : Andreas Gottschalk | |

It is certified that error appears in the above-identified patent and that said Letters Patent is hereby corrected as shown below:

Title Page, item 54, and col. 1, line 1, Change Title from "PERISTALTIC PUMP" to --PUMP DEVICE--.

At Column 6, Line 27, Below "thickness." insert --BRIEF DESCRIPTION OF THE DRAWINGS--.

At Column 6, Line 38, Delete "another in an offset manner," and insert the same on line 37 after "to one" as a continuing paragraph.

At Column 6, Line 41, Change "shaft." to --shaft,--.

At Column 9, Line 19, Change "180° ," to --180°,--.

Signed and Sealed this
Twenty-second Day of May, 2012

David J. Kappos
*Director of the United States Patent and Trademark Office*